(12) United States Patent
Koehler et al.

(10) Patent No.: US 9,610,096 B2
(45) Date of Patent: Apr. 4, 2017

(54) METHODS AND DEVICES FOR THE PREVENTION OF INCISIONAL SURGICAL SITE INFECTIONS

(71) Applicants: Prescient Surgical, Inc., Mountain View, CA (US); The Leland Stanford Junior University, Palo Alto, CA (US)

(72) Inventors: Jeremy Koehler, Menlo Park, CA (US); Jonathan Coe, Mountain View, CA (US); Insoo Suh, San Francisco, CA (US)

(73) Assignees: Prescient Surgical, Inc., San Carlos, CA (US); The Leland Stanford Junior University, Palo Alto, CA (US)

( * ) Notice: Subject to any disclaimer, the term of this patent is extended or adjusted under 35 U.S.C. 154(b) by 0 days.

(21) Appl. No.: 15/194,787

(22) Filed: Jun. 28, 2016

(65) Prior Publication Data
US 2016/0338730 A1 Nov. 24, 2016

Related U.S. Application Data

(63) Continuation of application No. 14/209,393, filed on Mar. 13, 2014, now Pat. No. 9,402,612.
(Continued)

(51) Int. Cl.
*A61B 1/32* (2006.01)
*A61B 17/34* (2006.01)
(Continued)

(52) U.S. Cl.
CPC ...... *A61B 17/3423* (2013.01); *A61B 17/0218* (2013.01); *A61M 1/0023* (2013.01);
(Continued)

(58) Field of Classification Search
CPC ........... A61B 17/0218; A61B 17/3423; A61M 1/0023
See application file for complete search history.

(56) References Cited

U.S. PATENT DOCUMENTS

| 4,537,680 A | 8/1985 | Barth |
| 4,942,700 A | 7/1990 | Hoberman et al. |

(Continued)

FOREIGN PATENT DOCUMENTS

| CA | 2183064 A1 | 8/1995 |
| WO | WO 2010/097477 A2 | 9/2010 |
| WO | WO 2014/151954 A2 | 9/2014 |

OTHER PUBLICATIONS

International search report and written opinion dated Oct. 3, 2014 for PCT/US2014/026723.
(Continued)

*Primary Examiner* — Ellen C Hammond
*Assistant Examiner* — Stuart S Bray
(74) *Attorney, Agent, or Firm* — Wilson Sonsini Goodrich & Rosati

(57) ABSTRACT

A surgical access device for facilitating access through an incision to a surgical site in a patient's body has a pliable membrane which is configured to engage and expand the incision. The pliable membrane includes a base layer, a permeable membrane attached to the base layer, and a fluid channel disposed between the layers. The fluid channel is fluidly coupled to a fluid source. The fluid is delivered to the surgical site via the permeable membrane. The surgical access device may also have a locking mechanism for holding the device in a desired configuration.

5 Claims, 16 Drawing Sheets

Related U.S. Application Data

(60) Provisional application No. 61/784,224, filed on Mar. 14, 2013.

(51) Int. Cl.
*A61M 1/00* (2006.01)
*A61B 17/02* (2006.01)

(52) U.S. Cl.
CPC ....... *A61M 1/0058* (2013.01); *A61B 17/0293* (2013.01); *A61B 17/3431* (2013.01); *A61B 2017/0225* (2013.01); *A61B 2017/3429* (2013.01)

(56) References Cited

U.S. PATENT DOCUMENTS

| | | | |
|---|---|---|---|
| 5,024,031 A | 6/1991 | Hoberman et al. | |
| 5,466,231 A | 11/1995 | Cercone et al. | |
| 5,486,183 A * | 1/1996 | Middleman | A61B 10/02 606/113 |
| 5,800,420 A | 9/1998 | Gross et al. | |
| 5,803,921 A | 9/1998 | Bonadio | |
| 6,371,968 B1 | 4/2002 | Kogasaka et al. | |
| 6,442,413 B1 | 8/2002 | Silver | |
| 6,730,020 B2 | 5/2004 | Peng et al. | |
| 7,279,208 B1 | 10/2007 | Goffena et al. | |
| 8,282,545 B1 | 10/2012 | Bodenstein | |
| 9,017,253 B2 | 4/2015 | Guralnik et al. | |
| 9,041,538 B2 | 5/2015 | Peeters | |
| 9,402,612 B2 | 8/2016 | Koehler et al. | |
| 2002/0013542 A1 | 1/2002 | Bonadio et al. | |
| 2003/0168068 A1 | 9/2003 | Poole et al. | |
| 2004/0054353 A1 | 3/2004 | Taylor | |
| 2004/0225193 A1 | 11/2004 | Krebs | |
| 2005/0209510 A1 | 9/2005 | Bonadio et al. | |
| 2005/0283050 A1 | 12/2005 | Gundlapalli et al. | |
| 2007/0261548 A1 | 11/2007 | Vrzalik et al. | |
| 2009/0054803 A1 * | 2/2009 | Saadat | A61B 1/0008 600/546 |
| 2009/0093752 A1 * | 4/2009 | Richard | A61B 17/3423 604/24 |
| 2009/0137984 A1 | 5/2009 | Minnelli | |
| 2010/0081880 A1 * | 4/2010 | Widenhouse | A61B 17/3462 600/201 |
| 2010/0094227 A1 * | 4/2010 | Albrecht | A61B 17/0293 604/167.01 |
| 2010/0100043 A1 * | 4/2010 | Racenet | A61B 17/3423 604/164.01 |
| 2010/0249516 A1 * | 9/2010 | Shelton, IV | A61B 17/0293 600/203 |
| 2010/0261972 A1 * | 10/2010 | Widenhouse | A61B 17/3462 600/206 |
| 2010/0312253 A1 * | 12/2010 | Nevyas-Wallace | A61F 9/007 606/107 |
| 2011/0021879 A1 * | 1/2011 | Hart | A61B 17/0293 600/207 |
| 2011/0054260 A1 * | 3/2011 | Albrecht | A61B 17/0218 600/208 |
| 2012/0022334 A1 * | 1/2012 | Piskun | A61B 1/05 600/208 |
| 2012/0203069 A1 * | 8/2012 | Hannaford | A61B 90/00 600/201 |
| 2013/0150681 A1 * | 6/2013 | O'Prey | A61B 17/0293 600/206 |
| 2013/0178709 A1 * | 7/2013 | Suh | A61B 17/0293 600/205 |
| 2013/0178710 A1 | 7/2013 | Suh et al. | |
| 2013/0184535 A1 | 7/2013 | Suh et al. | |
| 2014/0046123 A1 * | 2/2014 | Connors | A61F 2/0027 600/31 |
| 2014/0066704 A1 * | 3/2014 | Blumenkranz | A61B 1/00154 600/103 |
| 2014/0316210 A1 * | 10/2014 | Koehler | A61B 17/0218 600/208 |
| 2014/0343366 A1 * | 11/2014 | Coe | A61B 17/0293 600/205 |
| 2015/0142049 A1 * | 5/2015 | Delgado | A61B 17/0057 606/216 |
| 2015/0238073 A1 * | 8/2015 | Charles | A61B 17/02 600/102 |
| 2015/0335322 A1 | 11/2015 | Galbierz et al. | |
| 2016/0242751 A1 * | 8/2016 | Bonadio | A61B 17/00234 |

OTHER PUBLICATIONS

Office action dated Jan. 26, 2016 for U.S. Appl. No. 14/209,393.
Notice of allowance dated May 26, 2016 for U.S. Appl. No. 14/209,393.
European search report and opinion dated Jul. 25, 2016 for EP Application No. 14769323.8.

* cited by examiner

METHODS AND DEVICES FOR THE PREVENTION OF INCISIONAL SURGICAL SITE INFECTIONS

CROSS-REFERENCE

The present application is a continuation of U.S. application Ser. No. 14/209,393, now U.S. Pat. No. 9,402,612, which is a non-provisional of, and claims the benefit of, US Provisional Patent Application No. 61/784,224 filed on Mar. 14, 2013; the entire contents of which are incorporated herein by reference

BACKGROUND OF THE INVENTION

Field of the Invention

The present application generally relates to medical devices, systems and methods, and more particularly relates to devices, systems and methods used to prevent surgical site infections.

Formerly known as "wound infection," surgical site infection (SSI) is generally defined by the Centers for Disease Control and Prevention (CDC) as an infection in the area of the surgical incision that occurs within 30 days of an operation. The CDC further subdivides SSI into two groups. The first group includes superficial and deep "incisional" SSI (ISSI). The second group includes "organ/space" SSI. These two groups appear to be somewhat different phenomena with respect to etiology, physiology, pathogenesis, clinical presentation, and treatment. Of note, the term "wound infection," as currently used in the medical colloquium, refers to and is more compatible with ISSI, as opposed to organ/space SSI.

ISSI affects approximately 3-4% of the more than 30 million operations performed in the U.S. each year. Although the state of current medical care has minimized the mortality associated with ISSI, the morbidity and associated costs to the healthcare system remain significant. On average, ISSI extends the length of an inpatient hospital stay by 9 days, as well as introduces the added necessity and costs of outpatient wound management, which can reach upwards of 10,000-45,000 U.S. dollars per patient. Estimates of the aggregate annual burden to the U.S. healthcare system exceed five billion U.S. dollars.

The diagnosis of SSI is usually made by a physician and is usually based on the clinical finding of various signs and symptoms of infection at the incisional site, such as pain, tenderness, swelling, redness, warmth, and purulent drainage. Various ancillary tests, such as microbial cultures or radiographic exams (e.g., computed tomography scans), can aid in the diagnosis. The length of treatment can extend for weeks or even months.

Obese patients are particularly vulnerable to developing wound infections, with a two to three fold increased risk relative to the overall population. This is at least partially due to the poor vascularization of subcutaneous fat, reducing the delivery of prophylactic intravenous (IV) antibiotics to the incision site. Furthermore, subcutaneous fat is an excellent media for the incubation of bacterial infection. With increasing rates of obesity worldwide, this will only further compound the problem of ISSI.

Another risk factor for the development of ISSI is the type of surgical procedure performed. For example, colorectal surgeries are associated with a baseline infection rate of 15-20%. This is a result of the contaminated nature of the procedure, as fecal contents are often released into the operative field when colon, small bowel, or rectum is cut. Furthermore, colorectal surgery involves the manipulation and removal of large organs (e.g. the colon), and consequently, large incisions are often required to perform the procedures. ISSI risk is directly correlated with the size of surgical incision used to perform the case. These risks are further compounded when combined with other risk factors such as obesity. For example, the rates of wound infections in obese patients undergoing colorectal surgery increase to upwards of 33%, representing a major burden to the healthcare system in terms of the quality and cost of services.

Prior surgical instruments and methods have been developed with the aim of reducing wound infections, yet the scope of the problem has not been reduced. Some solutions have addressed the issue by implanting degradable sponges in the incision to combat the development of wound infections post-operatively. However, this approach led to increases in wound infection rates, as the immune system reacts poorly to the implant because the implant is a "foreign body."

Surgeons have previously irrigated the incision or wound margins with fluids such as saline and/or antibiotics, but the practice has proved to be disruptive to surgical progress, difficult to implement and standardize in surgical practices, and consumes valuable time, increasing patient risk and increasing operative costs.

Barrier wound protectors have also been employed to prevent the egress of bacteria into the incision, but this is merely a passive approach, and considering the barrier protection must be removed to complete the operation, the incision is inevitably exposed to the infectious contents contained within the surgical field. Additionally, wound protectors may be difficult to manipulate, especially when positioned in the surgical field. A further drawback is that the barrier can also trap bacteria onto the wound surface, allowing bacteria to proliferate in the wound space.

Considering the significant morbidity and cost associated with SSI, it is desirable to provide a way to reduce the occurrence of SSI that is superior to the limitations of currently available commercial devices.

In addition to the challenges mentioned previously, in select situations, a key aspect of surgery involves obtaining adequate surgical "exposure," or alternatively, adequate visualization and access to target anatomical landmarks and structures to be operated upon. To achieve proper exposure, surgeons can use a variety of surgical retractors generally configured to maximize the opening of the incision and create space within the operative region (e.g. chest, abdomen, orbit, neck, and groin) to facilitate the completion of the surgical procedure.

One surgical retractor used in abdominal surgery involves a top ring, bottom ring, and flexible tubular sheath disposed between the top and bottom rings. In numerous embodiments, manipulation of the top ring in a variety of ways (e.g., by rolling the sheath around the top ring) is sometimes effective to shorten the sheath length and retract the edges of the incision. In many cases, such surgical retractors incorporate barrier wound protection, the potential disadvantages of which have already been described.

The drawbacks of surgical retractors described in currently available commercial devices are numerous. They can be difficult to use, requiring additional time and the manual application of forces that may be difficult for surgeons to apply in an operative setting. They may require more than one person to operate, decreasing focus on the operative field, increasing operative time and personnel costs. In addition, due to the unpredictable nature of a surgical operation, the initial incision size may not be ideal, thus requiring lengthening during the course of the procedure. Many commercially available surgical retractors do not allow for an increase in incision size with the device in situ. Moreover, currently available commercial surgical retractors may employ a design requiring a variety of sizes to accommodate the wide range of incision sizes encountered during surgery. As a result, hospitals may have to stock a range of device sizes, and often multiple devices are used in a single procedure as the size of the incision may be increased. Using multiple devices may result in increased healthcare costs, surgery duration, and infections.

As noted previously, it may be advantageous to incorporate the combined functions of fluid delivery and fluid removal into a retraction device configured to reduce the risk of surgical site infections. Proposed embodiments of such a device may provide fluidic functions that are generally disposed along or near a pliable membrane, and that are configured to provide barrier wound protection (preventing direct contamination of the wound edges) and retraction of the surgical wound to permit visualization and access to the surgical site.

While these devices are promising, in certain circumstances, they can suffer from a few minor drawbacks including:

1) The necessity of cumbersome fluid delivery and fluid removal tubes placed within or about the wound margins (which may be prone to kinking in these tight spaces).
2) The unpredictable/uncontrolled locations of the fluid delivery and fluid removal elements, potentially leading to fluid delivery outside of the wound (either intra-abdominally or on the skin), which is undesirable.
3) The additional or separate component requirements for constructing the fluid delivery and/or fluid removal components, increasing manufacturing cost and/or difficulty.

Therefore, it would be desirable to provide improved surgical devices that address SSI. Such devices and methods of use preferably are easier to use, optimize fluid management within the surgical wound, and reduce manufacturing costs and complexity. At least some of these objectives will be met by the embodiments disclosed below.

SUMMARY OF THE INVENTION

The present invention generally relates to medical systems, devices and methods, and more particularly relates to surgical devices, systems and methods of use for reducing surgical site infections.

A preferred embodiment utilizes an integrated pliable membrane design that provides a barrier for wound protection and that may directly incorporate fluid delivery and removal in a single assembly.

In a first aspect of the present invention a surgical access device for facilitating access through an incision to a surgical site in a patient's body comprises a pliable membrane. The pliable membrane has a superior end and an inferior end, a base layer, a permeable membrane attached to the base layer and a fluid channel. The pliable membrane is configured to engage and expand the incision. The fluid channel is disposed between the base layer and the permeable membrane, and the fluid channel is fluidly coupled to a fluid source. Fluid from the fluid source is delivered to the surgical site via the permeable membrane.

The device may further comprise an intermediate layer of material disposed between the base layer and the permeable membrane. The intermediate layer of material may be foam. The device may further comprise a manifold seal layer of material disposed between the base layer and the permeable membrane. The manifold seal layer of material may capture the intermediate layer of material between the manifold seal layer and the base layer.

The base layer may be impermeable and the permeable membrane may comprise a plurality of holes disposed therethrough. The device may further comprise a superior retention member coupled to the superior end of the pliable membrane. The superior retention member may be radially expandable and radially collapsible. The superior retention member may form a closed ring. The device may further comprise an inferior retention member that is coupled to the inferior end of the pliable membrane. The inferior retention member may be resilient and may form a closed ring. The superior end of the pliable membrane may comprise a plurality of tabs each having a holes disposed therethrough, and the hole may be configured to be coupled with an engagement element on the superior retention member. The pliable membrane may form a substantially frustoconical shape. The pliable membrane may have a fixed length.

The device may further comprise a suction channel disposed between the base layer and the permeable membrane, and the suction channel may be configured to be coupled to a vacuum source. Vacuum from the vacuum source may draw fluid from the surgical site into the suction channel via the permeable membrane. The suction channel and the fluid channel may comprise a plurality of channels, and the channels may be positioned along the pliable membrane so as to substantially minimize fluidic resistance at a respective exit point. The plurality of channels may comprise a plurality of inner suction channels and a plurality of outer suction channels.

The permeable membrane may comprise a plurality of holes disposed therethrough, and the plurality of holes may comprise a first plurality of holes and a second plurality of holes. The first plurality of holes may be the holes through which the vacuum is applied, the second plurality of holes may be the holes through which the fluid passes. The second plurality of holes may be smaller than the first plurality of holes.

In another aspect of the present invention, a method for accessing a surgical site through an incision in a patient's body comprises providing a pliable membrane having a superior end, an inferior end, a base layer and a permeable membrane coupled to the base layer and inserting the pliable membrane through the incision into the surgical site. The method also may include radially expanding the pliable membrane thereby expanding the incision, and irrigating the surgical site with fluid delivered from a fluid channel disposed between the base layer and the permeable membrane. The fluid may exit a plurality of holes that are disposed in the permeable membrane.

A resilient inferior retention member may be coupled to the inferior end of the pliable member, and inserting the pliable membrane may comprise inserting the resilient inferior retention member through the incision into the surgical site. Radially expanding the pliable membrane may comprise forming the pliable membrane into a substantially frustoconical shape. Radially expanding the pliable membrane may comprise radially expanding a superior retention member that is coupled to the superior end of the pliable membrane. The method may further comprise maintaining a fixed length of the pliable membrane. The method may also comprise suctioning fluid from the surgical site. The suctioned fluid may enter a plurality of holes that are disposed in the permeable membrane and that pass through a suction channel disposed between the base layer and the permeable membrane.

In another aspect of the present invention, a method for fabricating a pliable membrane for a surgical access device configured to facilitate access through an incision to a surgical site in a patient's body comprises providing a base layer, a permeable membrane and optionally an intermediate layer of material. The intermediate layer of material may optionally be disposed between the base layer and the permeable membrane. The method also may comprise sealing the base layer to the permeable membrane, forming a first plurality of holes in the permeable membrane, and forming a fluid channel disposed between the base layer and the permeable membrane. The fluid channel may be configured to deliver a fluid from a fluid source through the fluid channel and to the surgical site via the first plurality of holes.

Sealing the base layer to the permeable membrane may comprise thermally welding the base layer to the permeable membrane. Forming the first plurality of holes may comprise laser drilling the first plurality of holes into the permeable membrane. The method may further comprise coupling an expandable superior retention member to a superior end of the pliable membrane. The superior end of the pliable membrane may comprise a plurality of tabs, and coupling the expandable superior retention member may comprise coupling the plurality of tabs with pins disposed on the superior retention member.

The method may further comprise coupling a locking mechanism to the superior retention member. The locking mechanism may comprise a ratchet and pawl having a locked configuration and an unlocked configuration. The locked configuration may be adapted to hold the superior retention member in a desired size, and the unlocked configuration may be adapted to allow expansion or collapsing of the superior retention member. The method may further comprise coupling a resilient inferior retention member to an inferior end of the pliable membrane. A second plurality of holes may be disposed in the permeable membrane, and the method may further comprise forming a suction channel disposed between the base layer and the permeable membrane. The suction channel may be configured to transmit a vacuum from a vacuum source through the suction channel to the surgical site via the second plurality of holes.

The method may further comprise providing a manifold seal layer of material, and disposing the manifold seal layer of material over the intermediate layer of material. The manifold seal layer may be sealed to the base layer, and the permeable membrane may be sealed to the manifold seal layer of material.

In still another aspect of the present invention, a surgical access device for facilitating access through an incision to a surgical site in a patient's body comprises a radially expandable and collapsible retention ring having a collapsed configuration, an expanded configuration, and a plurality of configurations therebetween. The retention ring comprises a plurality of links pivotably coupled to one another, and a locking mechanism having a locked position and an unlocked position. The locked position is configured to hold the retention ring in a desired configuration, and the unlocked position is configured to allow radial expansion or radial collapsing of the retention ring. The locking mechanism comprises a ratchet and a pawl. Engagement of the ratchet and pawl prevents pivoting of adjacent links amongst the plurality of links relative to one another. Disengagement the ratchet from the pawl allows pivoting of the adjacent links relative to one another. The locking mechanism maintains a distance between any two points on any two links in the plurality of links when the locking mechanism is in the locked position. Or, the locking mechanism maintains an angle between any two links in the plurality of links when the locking mechanism is in the locked position.

The retention ring may form a closed ring having a desired size in between the collapsed configuration and the expanded configuration. The locking mechanism may hold the closed ring in the desired size. The plurality of configurations may comprise between 2 and 20 configurations, or the plurality of configurations may comprise an infinite number of configurations.

Adjacent links in the plurality of links may be pivotably coupled together with a pin. A distance between two adjacent pins may be minimized in the collapsed configuration, and the distance may be maximized in the expanded configuration. An angle between the adjacent links may be minimized in the collapsed configuration, and the angle may be maximized in the expanded configuration.

The ratchet may comprise one or more teeth and the pawl may comprise one or more teeth. The one or more teeth of the ratchet may engage the one or more teeth of the pawl in the locked configuration. The one or more teeth of the ratchet or the one or more teeth of the pawl may be angled relative to one another so as to bias engagement therebetween when a collapsing force is applied to the adjustable ring.

The device may further comprise a torsion spring coupled to the pawl and configured to provide a torque in a direction that biases the pawl to engage the ratchet. The device may also comprise an interface surface coupled to the pawl. The interface surface may be configured to allow a user to apply a torque thereto thereby disengaging the pawl from the ratchet and allowing the retention member to expand or collapse.

The ratchet may comprise a continuous curved element frictionally engaged with the pawl. Frictional engagement of the continuous curved element and pawl may prevent pivoting of the adjacent links relative to one another. Disengagement of the continuous curved element from the pawl may allow pivoting of the adjacent links relative to one another to form an infinite number of configurations sized between the expanded and the collapsed configurations. The device may further comprise a torsion spring coupled to the pawl and configured to provide a torque in a direction that biases the pawl to frictionally engage the continuous curved element. The device may further comprise a cam surface configured to control rotation of the pawl by engagement with a portion of the adjustable ring. A pliable membrane may be coupled to the retention ring. An inferior resilient retention ring may be coupled to the pliable membrane opposite of the retention ring.

In still another aspect of the present invention, a method for accessing a surgical site through an incision in a patient's body comprises providing an access device having an adjustable superior retention member, an inferior resilient retention member and a pliable membrane coupled therebetween, and inserting the resilient retention member through the incision into the surgical site. The method also comprises inserting the pliable membrane through the incision into the surgical site, expanding or contracting the adjustable superior retention member outside the body to a desired size, and locking the adjustable superior retention member into the desired size with a ratchet and pawl locking mechanism.

The method may further comprise unlocking the adjustable superior retention member by disengaging the pawl from the ratchet and collapsing the adjustable superior retention member to a collapsed size smaller than the desired size. The method may include irrigating the surgical site with fluid delivered from the pliable membrane. The method may further comprise suctioning fluid from the surgical site with a vacuum provided by the pliable membrane.

These and other embodiments are described in further detail in the following description related to the appended drawing figures.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Specific embodiments of the disclosed device, delivery system, and method will now be described with reference to the drawings. Nothing in this detailed description is intended to imply that any particular component, feature, or step is essential to the invention.

The present invention will be described in relation to the deployment of the device during abdominal surgery. However, one of skill in the art will appreciate that this is not intended to be limiting, and the devices and methods disclosed herein may be used in other anatomical areas and in other surgical procedures.

Figure 1:
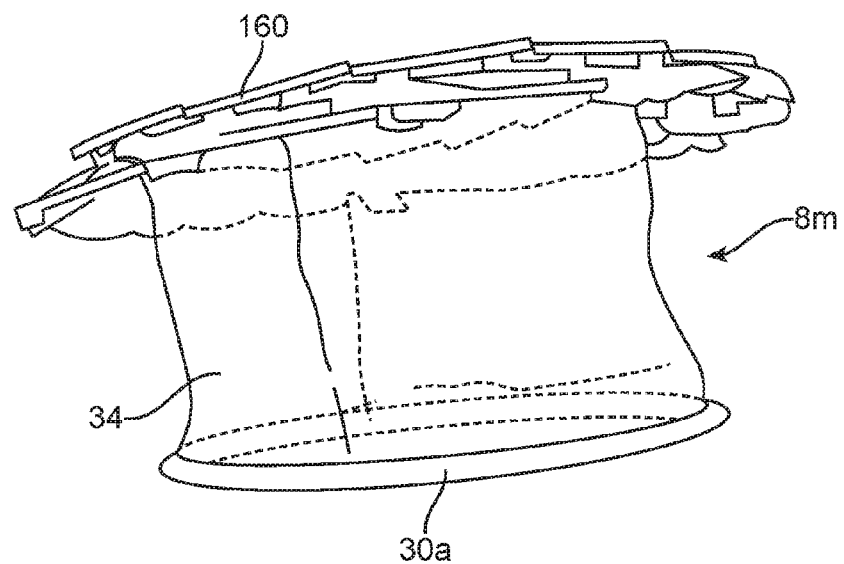
FIG. 1 illustrates a perspective view of an exemplary device for prevention of surgical site infections.

FIG. 1 shows an exemplary embodiment of a surgical device that may be used to prevent SSI. The surgical device 8m comprises an expanding linkage structure 160 (also referred to as a retraction ring or superior retention member), a pliable membrane 34 and a retention ring 30a (also referred to as an inferior retention member). The surgical device 8m may be used to provide retraction of a surgical wound for surgical access as well as irrigation and suction. Additional details about the surgical device and how it may be used are disclosed in U.S. patent application Ser. Nos. 13/736,904; 13/736,888; and 13/736,875; the entire contents of which are incorporated herein by reference. Additional details about the expanding linkage structure 160 and the pliable membrane 34 are disclosed below.

Figure 2:
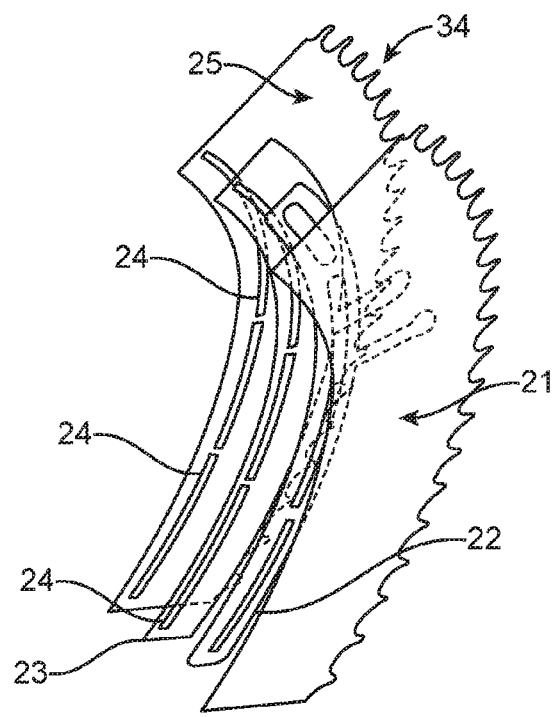
FIG. 2 illustrates an exploded view of the pliable membrane in the device of FIG. 1.

Pliable Membrane:

FIG. 2 illustrates an exploded view of a preferred embodiment of the pliable membrane 34. The pliable membrane 34 may comprise several layers of material laminated together. The pliable membrane 34 includes a base layer such as impermeable layer 21, a foam manifold 22, a foam manifold seal layer 23 and a semi-permeable layer 25. Suction windows 24 are disposed in the semi-permeable layer 25 and the foam manifold seal layer 23. Assembly of the layers forms an integrated pliable membrane design that overcomes at least some of the challenges previously described above.

Figure 3:
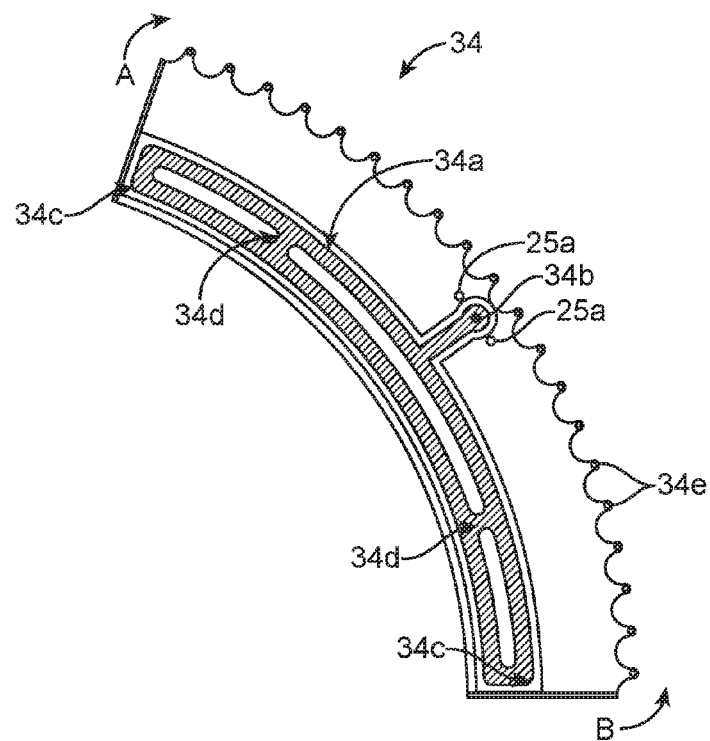
FIG. 3 illustrates a front view of the pliable membrane in FIG. 2.

FIG. 3 illustrates a front-on view of the pliable membrane 34, which in this exemplary embodiment is constructed on a flat plane. It will be appreciated that the assembly described in FIG. 2 can be constructed into a generally cylindrical or frustoconical assembly by attaching end "A" to end "B" as illustrated by the arrows. With the assembly seen in FIG. 2, attaching ends "A" and "B" together results in a generally cylindrical or frustoconical shape having the specific characteristics of a frustum. As described previously, a resiliently deformable ring may be sealed about the bottom perimeter of this structure. The deformable ring is configured to be placed preferably intra-abdominally during use, and may have any number of sizes, but preferably is sized to prevent the ring from popping out of the wound.

The pliable membrane assembly 34 includes several integrated features including connection tabs 34e, a suction manifold assembly 34a and a fluid delivery assembly which has inner conduits 34d and outer conduits 34c.

The connection tabs 34e may be configured to be connected to pivots (preferably inner pivots) of the upper expanding linkage structure 160. The connection tabs 34e include holes sized to be assembled around post features incorporated into the links comprising the retracting ring design described in this specification. The holes can be reinforced to prevent ripping or tearing of the pliable membrane at the attachment points, for example, by welding polyurethane (TPU) rings around the perimeter of the holes. The tabs may have a scalloped shape between subsequent attachment holes, and this shape permits predictable folding and collapse of the pliable membrane when the retraction ring is collapsed.

The suction manifold assembly 34a is preferably designed to remove fluid from the surgical site and includes a suction connection 34b that may be connected to a source of vacuum. The suction manifold may be defined by the enclosed space created between the foam manifold seal layer 23 and the impermeable layer 21 when these components are sealed around the foam manifold 22. A hole in the foam manifold seal layer 23 provides fluid communication between the suction manifold and an external suction source (e.g. medical suction) via a suitable fluidic connection such as a barbed elbow connector. Suction windows disposed in both the semi-permeable membrane and foam manifold seal layer provide fluidic communication with the surgical site, permitting removal of fluids therethrough.

Figure 4:
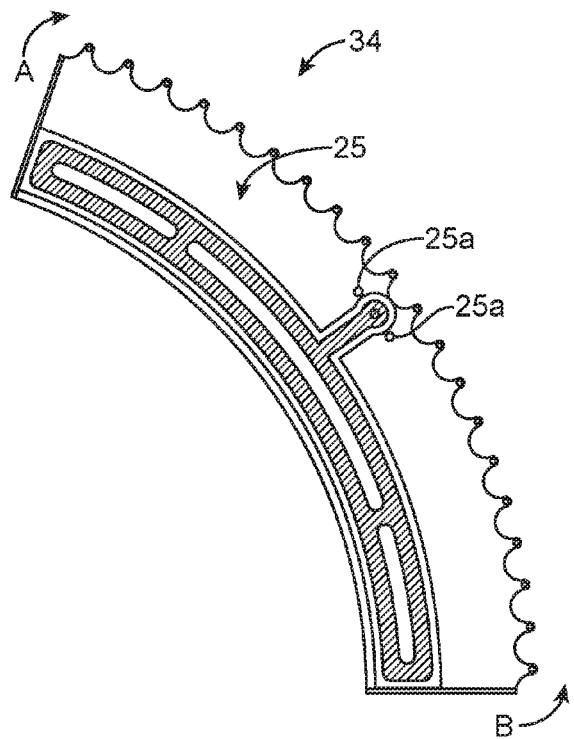
FIG. 4 is a front view and illustrates additional features of the pliable membrane in FIG. 2

The geometry design of the foam manifold may be balanced and this is seen in FIG. 4. In order to balance the level of suction provided at each location along the arc length (or alternatively when the assembly is formed into a generally cylindrical shape, the perimeter) of the suction windows, it is desirable to balance or equalize the fluidic resistance between the suction connection and each point along the arc length (or perimeter) of the suction windows. As fluidic resistance is proportional to conduit length, this can be accomplished by choosing the position of inner conduits 34d such that the fluidic resistance, R, is minimized for all points along the arc length (or perimeter if a cylinder) of the suction windows and the difference between the maximum R ($R_{max}$) and minimum R ($R_{min}$) along the arc length (or perimeter) of the suction windows is also minimized, with:

$$\frac{1}{R} = k \left[ \frac{1}{L_1} + \frac{1}{L_2} + \frac{1}{L_3} \cdots \frac{1}{L_n} \right]$$

Where k is a constant that depends on the geometry and material composition of the foam manifold and $L_1$, $L_2$, $L_3$, . . . , $L_n$ are the lengths of each the individual paths connecting the suction connection to a particular point along the suction windows. Also of note is the location of the suction windows to optimize fluid removal. If placed too low (towards the center of the arcs in FIG. 2, or alternatively, towards the bottom ring of the frustum described previously), the suction will be applied intra-abdominally. If placed too high, the wound or surgical site will be insufficiently covered with the fluid provided by the fluid delivery assembly, and in extreme cases, may even be exposed to the skin surface. In a preferred embodiment, the suction windows are preferably disposed in a location within 0"-2" of the bottom ring of the frustum. Other preferable locations will be apparent to one skilled in the art depending on patient body habitus and intended incision size.

FIG. 4 is a front view of the pliable membrane 34 and highlights features of the fluid delivery assembly which is designed to deliver a fluid such as saline or an antibiotic to the surgical site. Manufacturing of the pliable membrane is described in greater detail below.

The fluid delivery assembly is defined by the enclosed space created between the semi-permeable membrane 25 and the foam manifold seal layer 23 and impermeable membrane 21 when these three components are sealed together. One or more holes 25a in the semi-permeable membrane provides fluid communication between the fluid delivery assembly and an external suction source (e.g. IV fluid bag) via a suitable fluidic connection (e.g. barbed elbow).

The semi-permeable membrane 25 is permeable (through small perforations created via laser-drilled, pin-rolled, microfracturing/microtearing, or other suitable processes known in the art), thus permitting transfer of fluid from inside the space defined between the foam manifold seal layer 23, impermeable inner layer 21, and the semipermeable layer 25 and into the wound space or surgical site.

Figure 5:
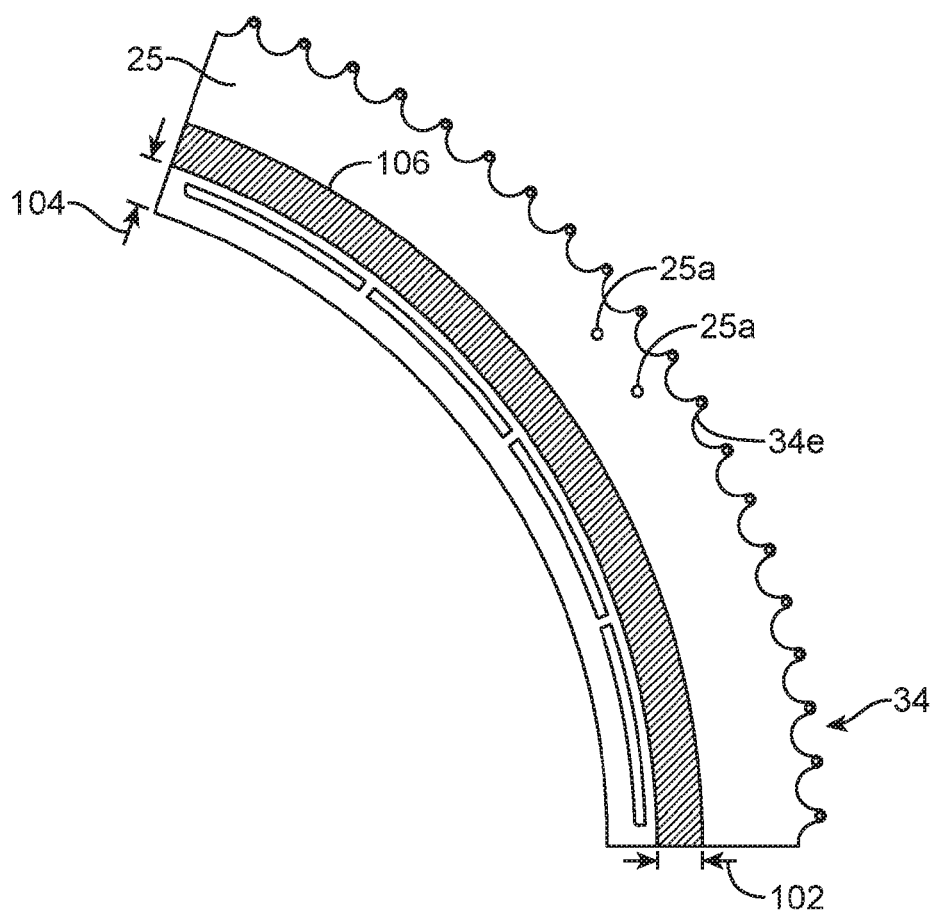
FIG. 5 illustrates the permeable region for fluid delivery in the pliable membrane.

FIG. 5 illustrates the permeable region 106 of the pliable membrane 34. The location of the permeable region optimizes fluid delivery to the surgical site. If placed too low (e.g. towards the center of the arcs in FIG. 1, or alternatively towards the bottom ring of the frustum described previously), the fluid is delivered intra-abdominally. If placed too high, fluid may undesirably be delivered to the skin surface.

In a preferred embodiment, the semi-permeable region 106 is approximately 1"-2" in width 102 and disposed in a location 104 within 1.5"-4" of the bottom ring of the frustum. Other preferable locations will be apparent to one skilled in the art depending on patient body habitus and intended incision size.

A preferred embodiment of the width 102 of the semi-permeable region is about 1.25 inches and it includes holes (not illustrated) having a diameter from about 0.005" to about 0.010" and the holes are dispersed in the semi-permeable region with a density of about 1-2 holes per square inch. The fluid communication holes 25a preferably have a 0.25" diameter elbow connector coupled thereto.

Fabrication:

FIGS. 6A-6D illustrate an exemplary method of fabricating the pliable membrane whereby the subsequent layers of the pliable membrane design are sealed using heat sealing, RF welding, or other suitable attachment means. Welded areas in each subsequent process step are highlighted by hatched regions or darkened lines. The foam manifold layer 22 is preferably comprised of reticulated (open-cell) polyurethane or polyethylene foam, and is approximately 0.125" thick. The other three layers 22, 23 and 25 of the design are preferably comprised of 0.003" thick TPU. Other manufacturing techniques, including re-arranging the order of the steps, eliminating the steps, or adding the steps described in FIGS. 6A-6D are also possible and will be apparent to one skilled in the art.

Figure 6A:
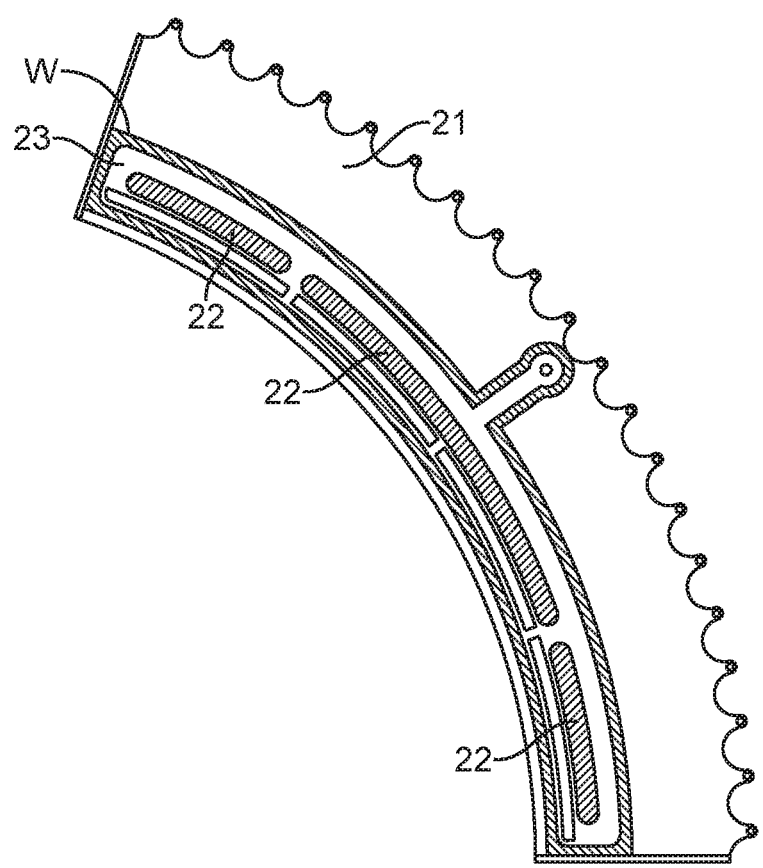
FIGS. 6A-6D illustrate an exemplary method of assembling the pliable membrane of FIG. 2.
Figure 6B:
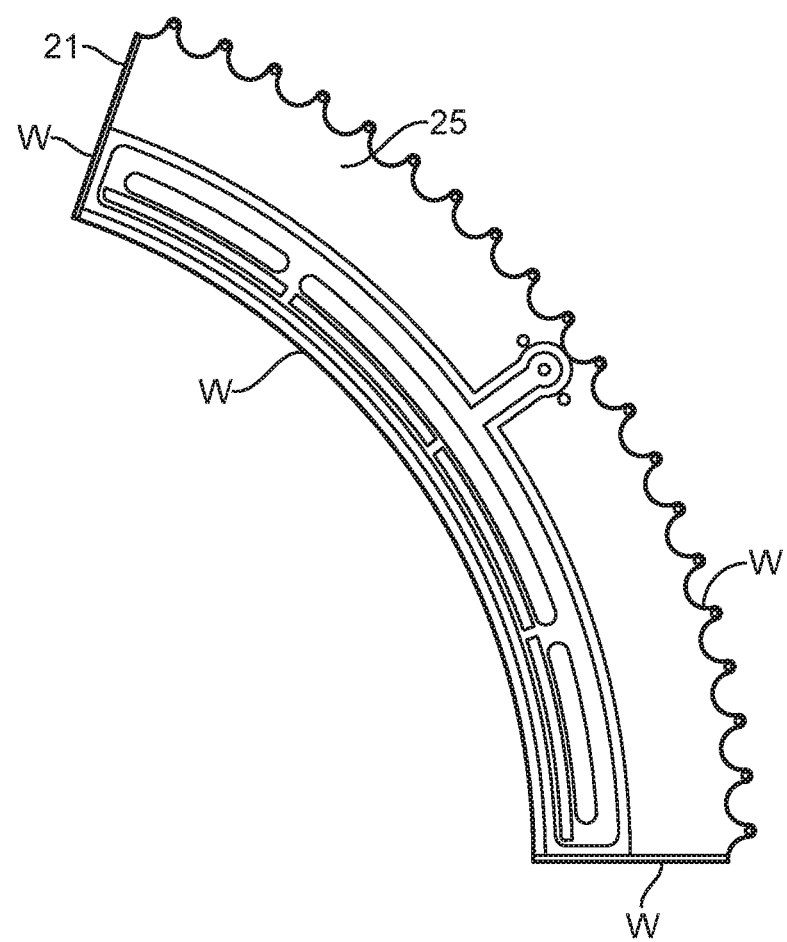
Figure 6C:
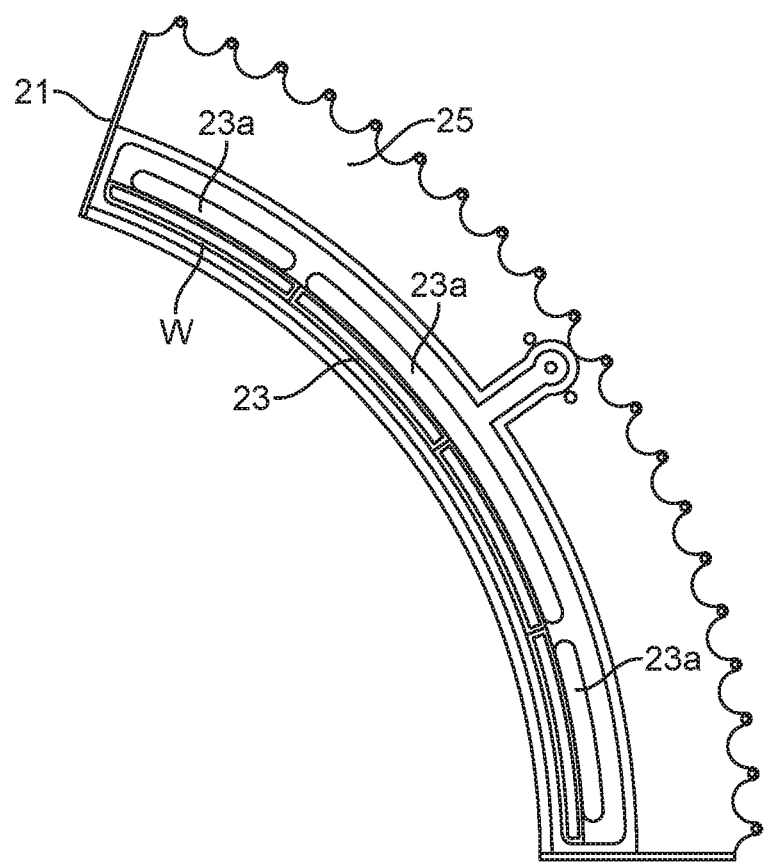
Figure 6D:
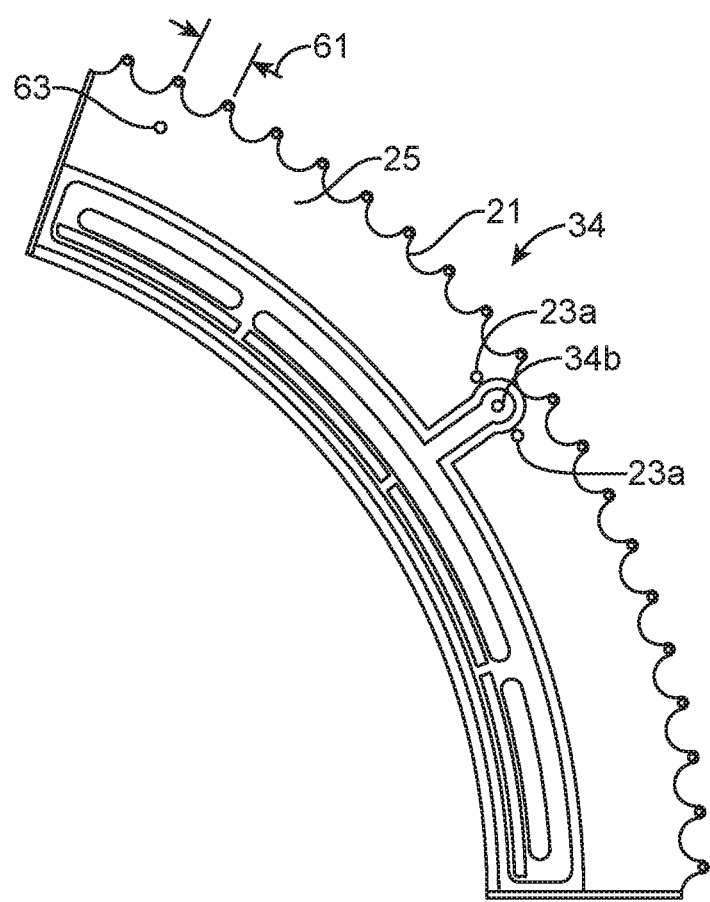

FIG. 6A illustrates welding W of the foam manifold layer 23 to the impermeable membrane 21 thereby capturing the foam manifold layer 22 therebetween. FIG. 6B illustrates welding W of the semi-permeable membrane 25 to the impermeable membrane 21 along the entire perimeter. FIG. 6C illustrates welding W of the semi-permeable membrane 25 to the foam manifold seal layer 23 around the suction windows 23a. In some circumstances, a barrier material may be required to prevent sealing all four layers of the pliable membrane together at these locations. FIG. 6D illustrates welding of pillow seals 63 in a grid pattern (not shown) to prevent billowing of the structure. The seal 61 in preferred embodiments is about 3.57 degrees and is repeated in a grid pattern defined by the intersection of connection points and approximately 1" concentric rings.

Sizing:

Wound sizing, determining the characteristics of the generally cylindrical shape or frustoconical shape, and optimizing the location of the suction windows and permeable region of the semi-permeable membrane may be estimated using the following exemplary model.

Figure 7A:
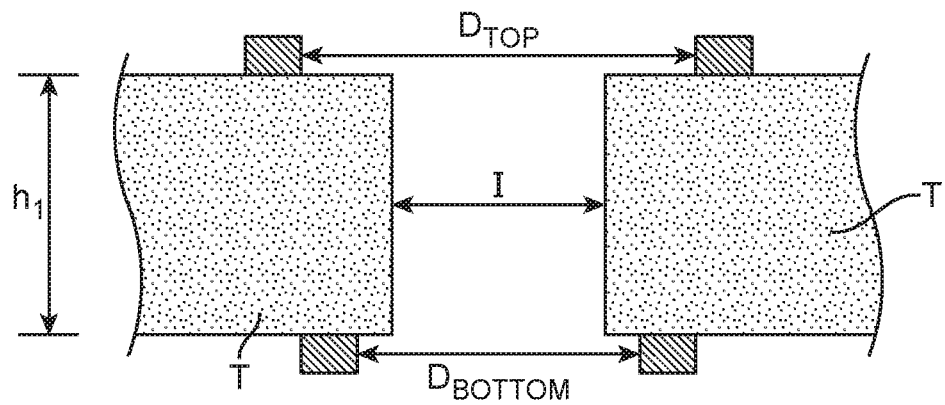
FIGS. 7A-7B illustrate characteristic dimensions of a surgical wound.
Figure 7B:
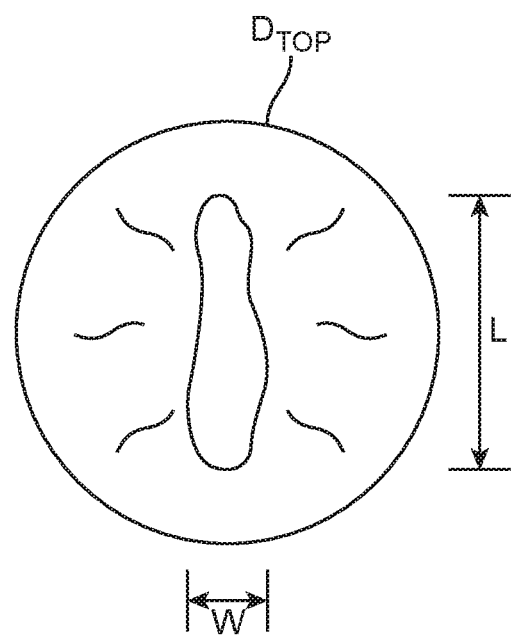

Without being bound by any particular theory, the shape of the pliable membrane when fully assembled, is preferably substantially cylindrical or frustoconical. One particular advantage of the retraction design disclosed in this specification is the ability to accommodate a wider range of incision sizes than other commercially available devices. The range of incision sizes that the presently disclosed device is compatible with depends on:

1) The maximum diameter of the top retraction ring, $D_{top}$
2) The diameter of the bottom ring, $D_{bottom}$, and which may be fixed or variable
3) The height of the pliable membrane, h (here, the perpendicular distance between top and bottom rings)
4) The patient body habitus $h_1$ (e.g. thickness of the abdominal wall)
5) Incision length, L These parameters are generally described in in FIGS. 7A-7B. FIG. 7A is a cross-section of a surgical site showing an incision I made in tissue T. The device of FIG. 1 is inserted into the wound such that the upper ring or retention member is superior to the incision and external to the body, while the lower ring or retention member is inferior to the incision and disposed in the patient. The pliable membrane is not illustrated for ease of viewing. The upper ring has diameter $D_{top}$, and the lower ring has diameter $D_{bottom}$, and thickness of the abdominal wall is $h_1$. FIG. 7B is a top view of the incision showing the incision length L and incision width w.

Thus, for a given $D_{top}$, $D_{bottom}$, and $h_1$, there is a range of incision sizes for which the proposed device will be compatible. Compatibility is constrained in one sense by the ability of the top ring to expand and take up slack in the pliable membrane, and in the other by the requirement that the top ring is at minimum at least as large as the incision opening (so as not to impede the surgery). Other assumptions in the proposed model include the assumption that the length of the incision is greater than or equal to the width of the incision (L≥w), and that $D_{top} \geq D_{bottom}$, and $D_{top}$ is greater than or equal to the length of the incision plus two centimeters, $D_{top} \geq L+2$ cm. The pliable membrane length is fixed.

Table 1 below is a design table that was constructed using these criteria and a preferred embodiment of the device with h=5", $D_{top}$=21.1 cm, and $D_{bottom}$=16 cm. The unshaded region corresponds to the range of incision sizes for which the device will be compatible. It will be apparent to one skilled in the art that adjusting these design parameters will result in a different target range for compatible incision sizes.

frustoconical shape described here provides a frustrum rolled in an edge-to-edge fashion but in reality, overlap of the edges is needed to perform the joining operation. An overlap is created by lengthening the sheet of material used to create the pliable membrane, which can result in small protrusions at the lap joint. Therefore small tabs may be created with angled ends that are a function of the frustrum angle to avoid protrusions.

TABLE 2

| Inputs | |
|---|---|
| Bottom Diameter | 6.29921260 in |
| Top Diameter | 8.3250000 in |
| h | 5 in |
| Length | 5.10156384 in |
| Outputs | |
| Radius_1 | 15.8633799 in |
| Radius_2 | 20.9649438 in |
| Included Angle | 1.25 rad |
| Included Angle | 71.48 degrees |
| tab angle | 0.20 rad |
| tab angle | 11.45193 degrees |

*** Top Diameter < Bottom Diameter

Expanding Linkage Structure Mechanisms:

In the course of using the device of FIG. 1, it could be advantageous to maintain a selected configuration of the expanding linkage structure 160 (also referred to as a retention member). The following exemplary embodiments

TABLE 1

| Incision Length [cm] | Habitus [cm] | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| 5 | 10.5 | 9.5 | 8.5 | 7.5 | 6.5 | 5.5 | 4.5 | 3.5 | 2.5 | 1.5 | 0.5 | 0.5 |
| 6 | 12 | 11 | 10 | 10 | 8 | 7 | 6 | 5 | 4 | 3 | 2 | 1 |
| 7 | 13.5 | 12.5 | 11.5 | 11.5 | 9.5 | 8.5 | 7.5 | 6.5 | 5.5 | 4.5 | 3.5 | 2.5 |
| 8 | 15 | 14 | 13 | 13 | 11 | 10 | 9 | 8 | 7 | 6 | 5 | 4 |
| 9 | 16.5 | 15.5 | 14.5 | 14.5 | 12.5 | 11.5 | 10.5 | 9.5 | 8.5 | 7.5 | 6.5 | 5.5 |
| 10 | 18 | 17 | 16 | 16 | 14 | 13 | 12 | 11 | 10 | 9 | 8 | 7 |
| 11 | 19.5 | 18.5 | 17.5 | 17.5 | 15.5 | 14.5 | 13.5 | 12.5 | 11.5 | 10.5 | 9.5 | 8.5 |
| 12 | 21 | 20 | 19 | 19 | 17 | 16 | 15 | 14 | 13 | 12 | 11 | 10 |
| 13 | 22.5 | 21.5 | 20.5 | 20.5 | 18.5 | 17.5 | 16.5 | 15.5 | 14.5 | 13.5 | 12.5 | 11.5 |
| 14 | 24 | 23 | 22 | 22 | 20 | 19 | 18 | 17 | 16 | 15 | 14 | 13 |
| 15 | 25.5 | 24.5 | 23.5 | 23.5 | 21.5 | 20.5 | 19.5 | 18.5 | 17.5 | 15.5 | 15.5 | 14.5 |
| 16 | 27 | 26 | 25 | 25 | 23 | 22 | 21 | 20 | 19 | 18 | 17 | 16 |
| 17 | 28.5 | 27.5 | 26.5 | 26.5 | 24.5 | 23.5 | 22.5 | 21.5 | 20.5 | 19.5 | 18.5 | 17.5 |
| 18 | 30 | 29 | 28 | 28 | 26 | 25 | 24 | 23 | 22 | 21 | 20 | 19 |
| 19 | 31.5 | 30.5 | 29.5 | 29.5 | 27.5 | 26.5 | 25.5 | 24.5 | 23.5 | 22.5 | 21.5 | 20.5 |
| 20 | 33 | 32 | 31 | 31 | 29 | 28 | 27 | 26 | 25 | 24 | 23 | 22 |
| 21 | 34.5 | 33.5 | 32.5 | 32.5 | 30.5 | 29.5 | 28.5 | 27.5 | 26.5 | 25.5 | 24.5 | 23.5 |
| 22 | 36 | 35 | 34 | 34 | 32 | 31 | 30 | 29 | 28 | 27 | 26 | 25 |

Once the generally cylindrical shape of the pliable membrane is calculated as described above, the shape needs to be "unwrapped" in order to determine the planar geometry in which the pliable membrane is constructed. This process is described below.

Figure 8A:
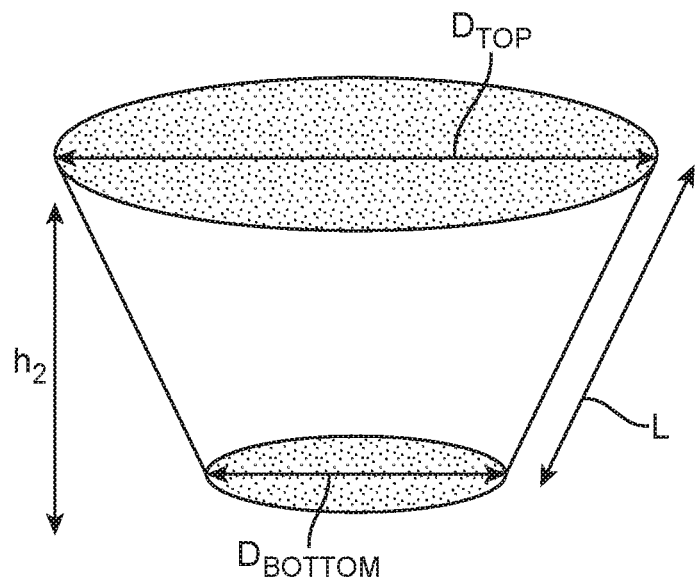
FIGS. 8A-8B illustrate a device sizing model.
Figure 8B:
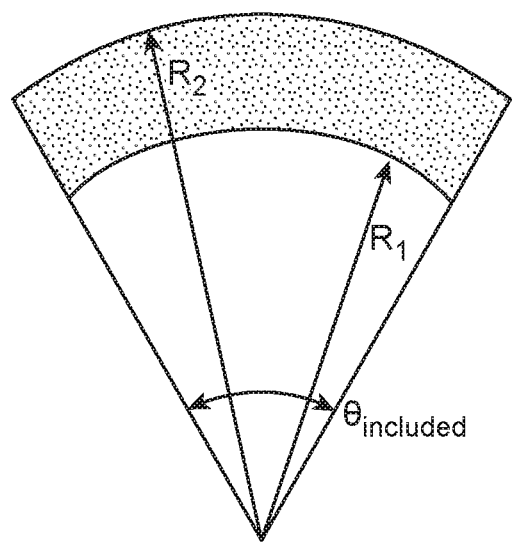

FIG. 8A illustrates the conical or frustoconical device and FIG. 8B illustrates the device once it has been cut and unrolled into a flat pattern. Table 2 below summarizes the calculations for an exemplary embodiment of a device where outputs of a wound sizing model (which define the geometry of a generally cylindrical shape) to the geometry of a planar construction of the pliable membrane. In this section, the height $h_2$ refers to the height of the pliable membrane and this is listed as h in Table 2. The fact that the illustrate mechanisms that may be used to maintain an intermediate configuration of the expanding linkage structure.

Figure 9:
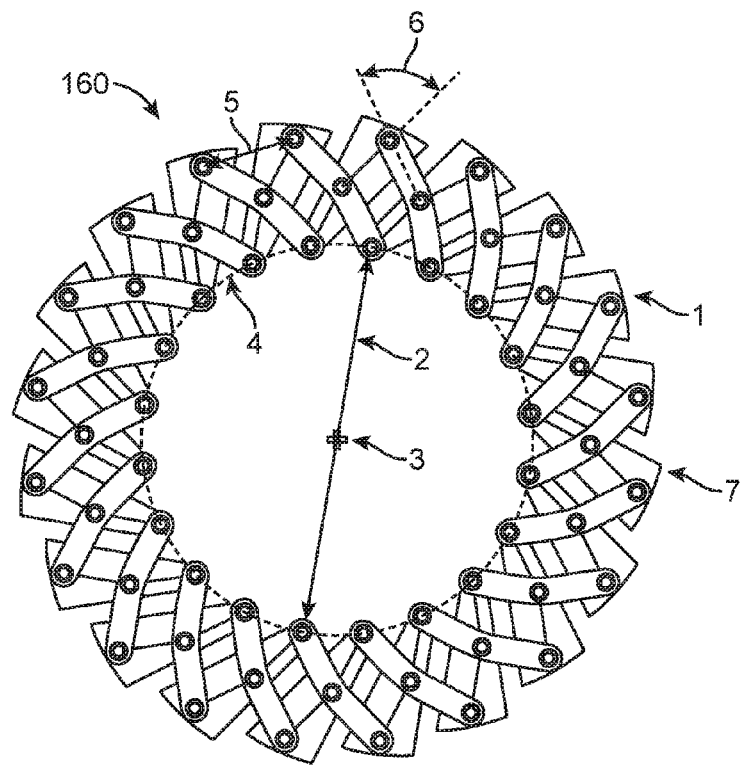
FIG. 9 illustrates an intermediate position of a retention ring.
Figure 10:
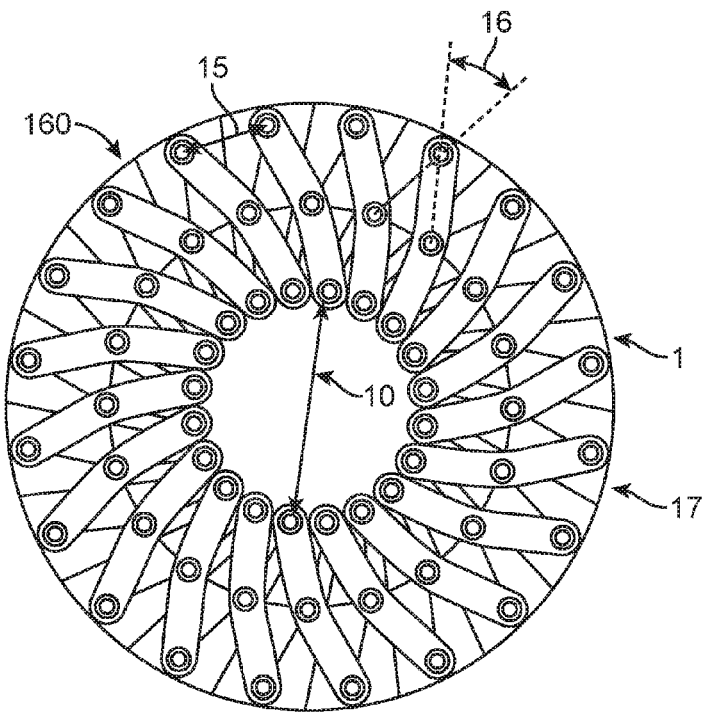
FIG. 10 illustrates a collapsed configuration of the device in FIG. 9.
Figure 11:
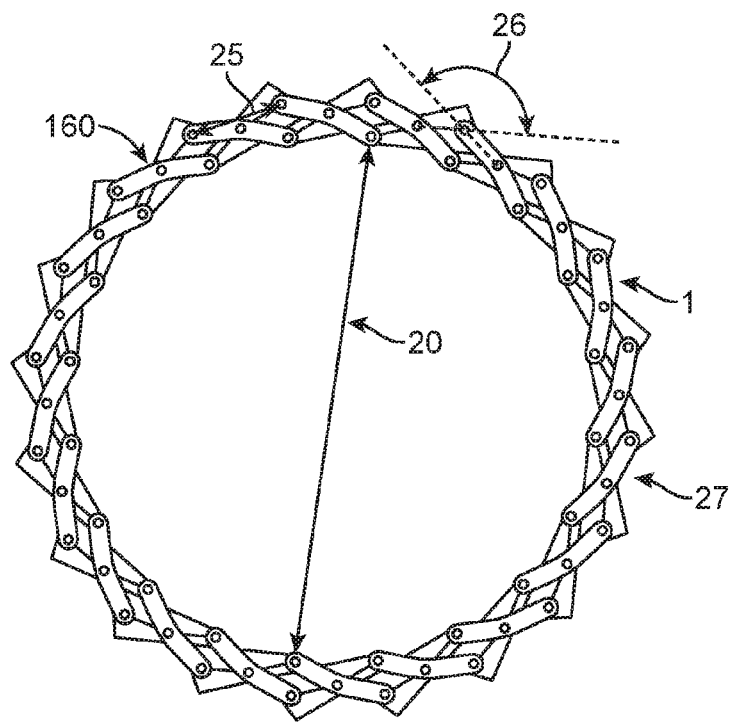
FIG. 11 illustrates an expanded configuration of the device in FIG. 9.

FIG. 9 shows the expanding structure 1 which may be manually expanded to an intermediate state 7 defined by an effective inner diameter defined by the distance of a line 2 connecting two inner posts and passing through the center 3 of a circle 4 intercepting the center of all of the inner posts, and that is greater than the minimum effective inner diameter 10 of a structure 1 when in a fully collapsed state 17 as seen in FIG. 10, and that is less than the maximum effective diameter 20 of a structure 1 in the fully expanded state 27 as illustrated in FIG. 11. Thus, the distance 2 in FIG. 9 is greater than the distance 10 in FIG. 10 and less than the distance 20 in FIG. 11.

With the wound retracted with the structure in an intermediate state, it can be advantageous for the structure to maintain the intermediate state so the surgeon or an assistant does not have to hold the structure to counteract the force the wound is placing on the pliable membrane, which is attached to the expanding structure 1. Due to the fact that the wound size will vary based on the procedure being performed, patient anatomy, and other factors, it could be beneficial for the structure to be able to selectively maintain one of a plurality of unique intermediate states defined by the effective inner diameter. This plurality of intermediate states may have any number of states such as between two and twenty unique states, three and fifteen unique states, four and twelve unique states, five and ten unique states, or six and eight unique states. Additionally, it may be advantageous to have an infinite number of unique states that can be selectively maintained.

Due to the fact that all of the links rotate with respect to each other and the central axis of the structure and all of the pivots translate, there are multiple mechanisms that can be used to selectively maintain an intermediate state 7 of structure 1. As shown in FIGS. 9-11, the distance 5 between two posts increases from a minimum distance 15 in a collapsed state 17 to a maximum distance 25 in an expanded state 27. Additionally, as shown in FIGS. 9-11, the angle 6 between two adjacent links increases from a minimum angle 16 in a collapsed state 17 to a maximum angle 26 in an expanded state 27. This fact is also true for any two links whose relative angle changes as a structure 1 changes state: the angle will only increase or decrease from a collapsed state 17 to an expanded state 27. Therefore, a mechanism to maintain a distance 5 between any two points on different links or an angle 6 between links of a structure 1 in an intermediate state 7 may be used.

Figure 12:
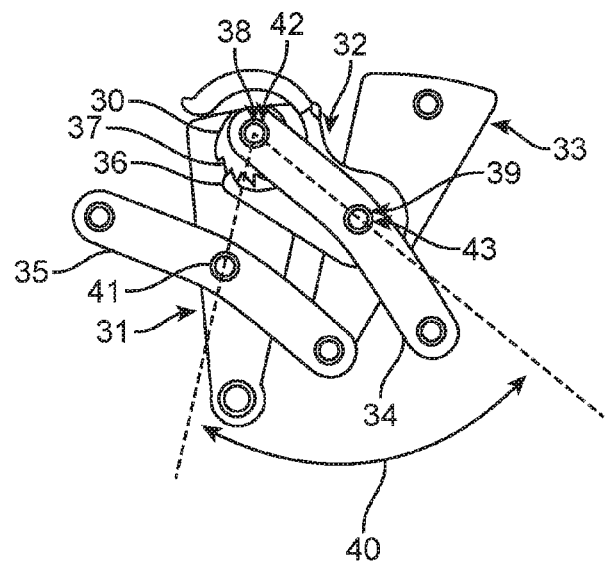
FIGS. 12-21 illustrate exemplary locking mechanisms for holding the device in FIG. 9 in a desired position.

FIG. 12 illustrates a first exemplary embodiment of a mechanism that maintains an angle 40 between two links. While this embodiment shows two adjacent links being used, one of skill in the art will appreciate that non-adjacent links may also be used. FIG. 12 and the other mechanism figures illustrate only a portion of the structure 1 for clarity.

A ratchet/pawl mechanism may be used with a ratchet 30 disposed about a post 38 on a first link 31 and a pawl 32 disposed about a post 39 on a second link 33. Third link 34 and fourth link 35 constrain the first 31 and the second 33 links to rotate in accordance with the full expanding structure as described previously. The ratchet 30 could be rotationally constrained by a post 38 with any profile that provides rotational constraint, such as a hexagonal, oval, or triangular profile. A pawl tooth 36 may engage a tooth 37 on the ratchet 30.

This engagement could prevent the links from rotating in a direction such that the angle 40 formed between lines connecting an outermost post 38 and middle post 41 of a first link 31 and an outermost hole 42 and a middle hole 43 of a third link 34 decreases. This decrease in angle 40 would be required for the effective inner diameter of the structure 1 to decrease. This mechanism would therefore selectively maintain an intermediate state as described previously. The ratchet 30 and pawl 32 members may be made from a plastic material such as polycarbonate (PC), polypropylene (PP), polyethylene (PE) or another material known to one skilled in the art. The members may be injection molded, milled, laser cut, or additively manufactured using such processes as Fused-Deposition Modeling (FDM) or other process known to those skilled in the art. Additionally, the ratchet 30 and pawl 32 members may be made from a metal material such as steel, stainless steel, aluminum, titanium, or another material known to know skilled in the art. The members may be injection molded, milled, laser cut, or additively manufactured using such processes as Fused-Deposition Modeling (FDM) or other process known to those skilled in the art.

Figure 13:
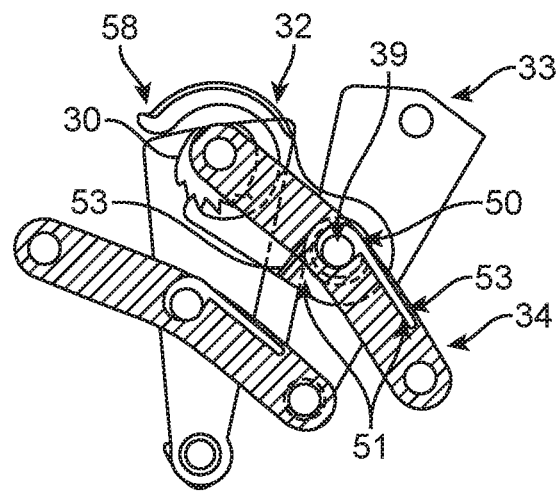

Additionally, as shown in FIG. 13, a torsion spring 50 may be disposed between the pawl member 32 and the third link 34 and about a post 39 and configured to provide a torque in a direction to cause engagement between the pawl member 32 and the ratchet member 30. Legs 51 of the torsion spring 50 may engage the pawl member 32 and the third link 34 in slots 52 (on the underside of the pawl member 32) and 53, respectively. The torque helps ensure successful engagement between the pawl 32 and ratchet 30 members by providing a torque that biases the pawl tooth 36 toward the ratchet tooth 37. In order to further promote engagement, the interface between pawl tooth 36 and ratchet tooth 37 may be angled relative to the center of rotation of the pawl 32 such that the normal force between the teeth is oriented in a direction that substantially causes the pawl 32 to rotate in a direction toward the ratchet 30. This could ensure that if contact were provided between the ratchet 30 and pawl 32, a force or moment applied to structure 1 that would result in a decrease in angle 40 would substantially serve to further engage the mechanism and prevent a further decrease in angle 40 if not fully engaged prior to the application of the force or moment.

Further, an interface surface 58 may be provided on the pawl member 32 to allow the user to engage the interface surface and substantially impart a torque counter to the torque provided by the torsion spring 50. The applied torque may serve to disengage the pawl tooth 36 from the ratchet tooth 37 and allow the angle 40 to decrease, which would allow the effective inner diameter 2 of structure 1 to decrease.

It will be apparent to one skilled in the art that ratchet tooth/teeth 37 may be replaced by a continuous curve (e.g. smooth profile) with a high friction interface with a pawl component 32 to prevent relative motion and, therefore, maintain an intermediate state of structure 1. The high friction surface may be defined on the interface surface between the ratchet 30 and pawl 32 components. With the inclusion of a torsion spring 50, a desired amount of friction force may be delivered by specifying a spring that provides a desired normal force between the two components which will result in a friction force resisting relative motion. It will be appreciated that this assembly provides an infinite number of intermediate configurations due to the fact that the frictional resistance force is present at every location in which contact is established. The interface surface 58 on pawl member 32 may be engaged to rotate pawl component 32 and eliminate contact and allow adjoined links to move and then be released to re-establish contact and maintain the current intermediate state. The curve on ratchet component 30 may be made from any material with a high coefficient of friction or may have any material with a high coefficient of friction added to it. The ratchet 30 component itself may have a rough surface (created by a sanding operation, blasting operation, peening operation, or any other means known to one skilled in the art) or have an additional surface, such as sandpaper, roughened metal or plastic, or other high friction material known to one skilled in the art, attached to the contact area. It will be appreciated that the frictional concept with an unlimited number of intermediate states may be utilized with either of the disclosed mechanisms.

Figure 14:
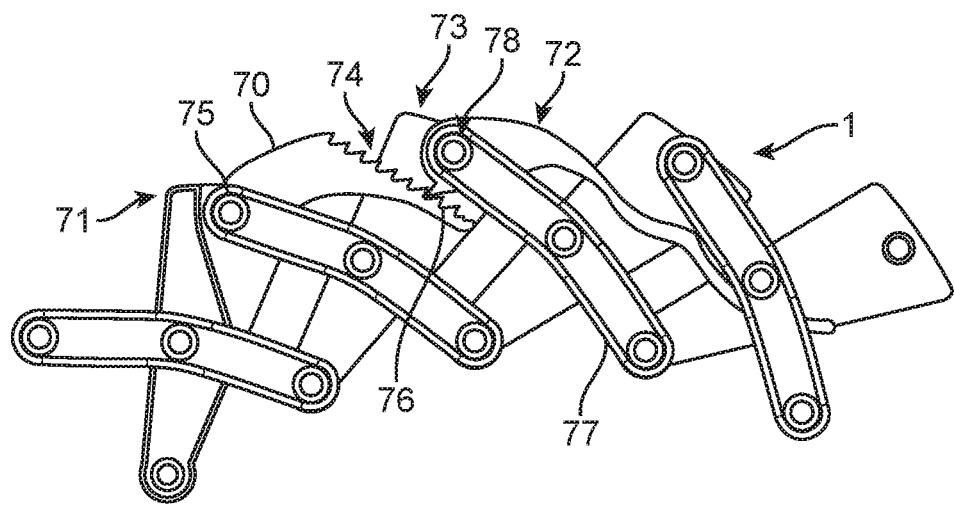

Another exemplary mechanism maintains the distance between two posts of two links as shown in FIG. 14, which does not show a full structure 1 in order to enhance the clarity of the figure. In this figure, two adjacent links and their outer posts are used, however, this is an arbitrary choice for illustrative purposes only. Any combination of posts may be used. A first engagement member 70 may be rotatably disposed about an outer post 75 of a first link 71 and a second engagement member 72 may be disposed about an outer post 78 of a second link 73. Second engagement member 72 may be rotationally constrained to third link 77 by any means capable of rotational constraint such as a pin through both members, an adhesive, or mating feature such as a boss. One or both engagement members 70 and 72 may be provided with one or more teeth 74 and 76.

Figure 15:
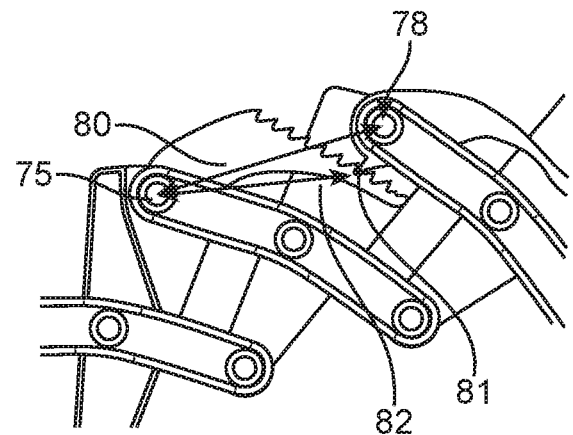

FIG. 15 shows that as structure 1 is expanded from a first collapsed state 17 to a second intermediate state 27, the distance 80 between the outer posts 75 and 78 of the first link 71 and the second link 73 increases. This distance increases from a minimum distance 15 in a fully collapsed state 17 to a maximum distance 25 in the fully expanded state 27. At a distance between the minimum distance 15 and the maximum distance 25, one or more teeth 74 on the first engagement member 70 may engage one or more teeth 76 on the second engagement member 72. Due to the fact that the end of tooth 76 on second engagement member 72 is provided at a fixed distance from post 78, the distance from the post 78 to a contact point 81 between first engagement member 70 and second engagement member 72 is constant. Therefore, constraining distance 82, the distance from post 75 to contact point 81, constrains distance 80. This mechanism is therefore capable of maintaining structure 1 in an intermediate state 7.

Figure 16:
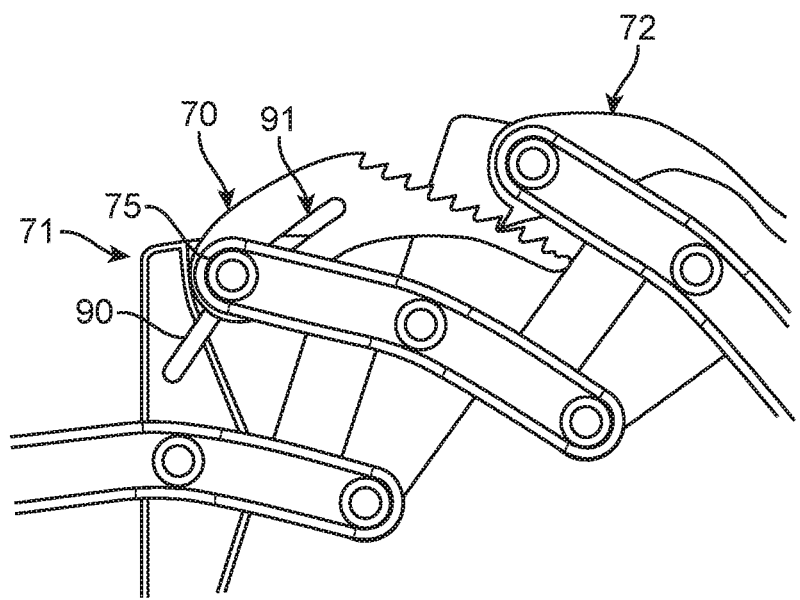

FIG. 16 illustrates another exemplary embodiment that uses a torsion spring to help engagement. The torsion spring may be disposed between the first engagement member 70 and first link 71 and configured to provide a torque in a direction to cause engagement between the first engagement member 70 and the second engagement member 72. A first slot 90 could be provided in a first link 71 and a second slot 91 could be provided in a first engagement member 70. The slots may accept the legs of a torsion spring disposed about post 75.

Figure 17:
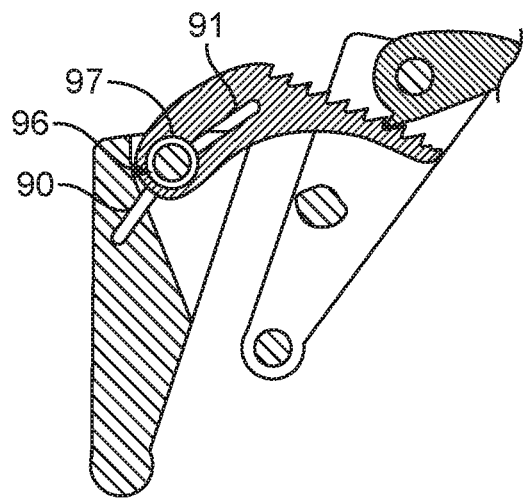

As shown in in the sectional view of FIG. 17, an amount of clearance 96 may be provided between the post 75 and a hole 97 in the first engagement member to capture the torsion spring. The torsion spring may provide a counter-clockwise torque to first engagement member 70 to ensure engagement between the first engagement member 70 and second engagement member 72.

Figure 18:
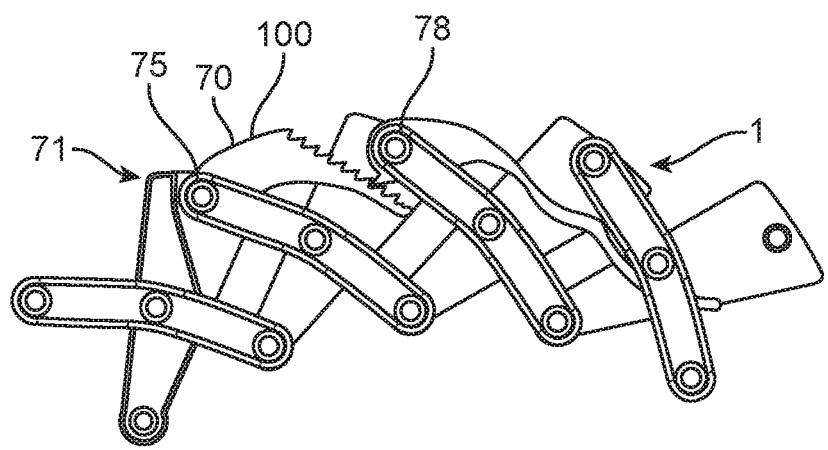

Additionally, as shown in FIG. 18, the first engagement member 70 may provide an interface surface 100 to allow a user or users to engage the interface surface 100 and impart a force and/or torque to disengage a first engagement member 70 and a second engagement member 72, which allows the distance 80 between a first post 75 and a second post 78 to change. Further, if a torsion spring is provided as previously described, the force and/or torque provided by the user could additionally counteract a torque provided by the torsion spring to disengage the first engagement member 70 and second engagement member 72.

Additionally, in order to further promote engagement, the interface between first engagement member 70 and second engagement member 72 could be angled relative to the center of rotation of the first engagement member 70 such that the normal force between a tooth 74 on first engagement member 70 teeth and a tooth 76 on second engagement member 72 could be oriented in a direction that substantially causes the first engagement member 70 to rotate in a direction toward the second engagement member 72. This may help ensure that if contact is provided between the first engagement member 70 and second engagement member 72 and an input force or moment is provided by a user to structure 1 in a direction or sense such that substantially causes structure 1 to move toward a state closer to a fully collapsed state 17 than a current state 7, the resultant force or moment applied to the first engagement member 70 from the second engagement member 72 may substantially serve to further engage the mechanism if not fully engaged prior to the application of the force or moment.

Figure 19:
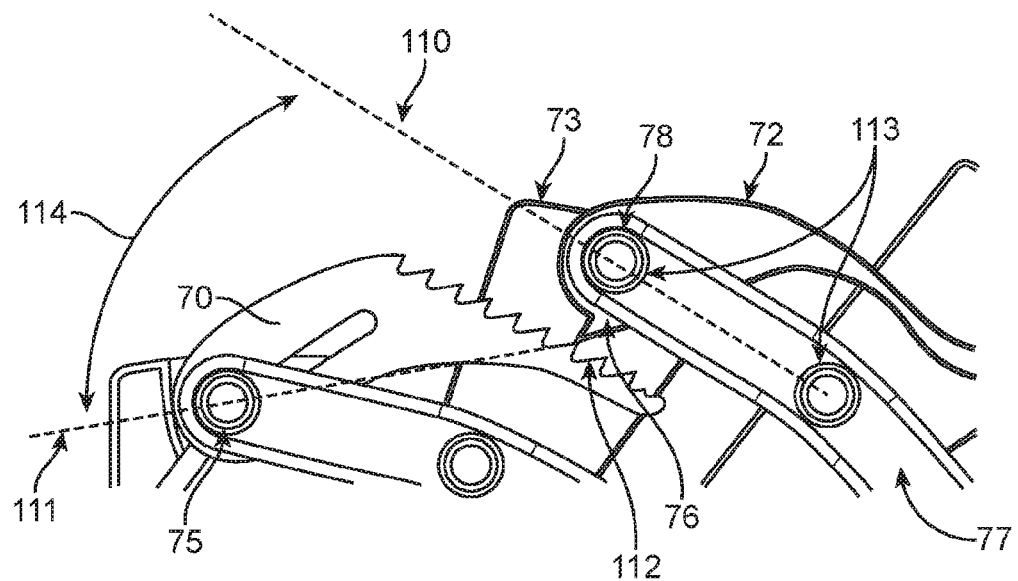

FIG. 19 illustrates another exemplary embodiment of a mechanism for holding the device in a desired configuration. Due to the fact that all of the links in structure 1 rotate and translate, an angle 114, defined as the angle created between a line 110 connecting two outer holes 113 of a third link 77 to which second engagement member 72 could be rotationally constrained as previously described and a line 111 connecting a contact point 112 between a first engagement member 70 and a second engagement member 72 and a post 75 about which the first engagement member 70 is constrained as shown in the figure, will change as second engagement member 72 rotates due to its rotation constrained to third link 77. This could make it difficult to provide a desirable engagement angle for self-engagement, as described previously, at all possible intermediate states. Therefore, it may be advantageous to allow second engagement member 72 to rotate about an outer pin 78 on a second link 73 and, therefore, change its orientation independent of third link 77 and account for the relative rotation of the links in structure 1 to provide a desired engagement angle between the first engagement member 70 and second engagement member 72 at all possible intermediate states 7 of structure 1.

Figure 20:
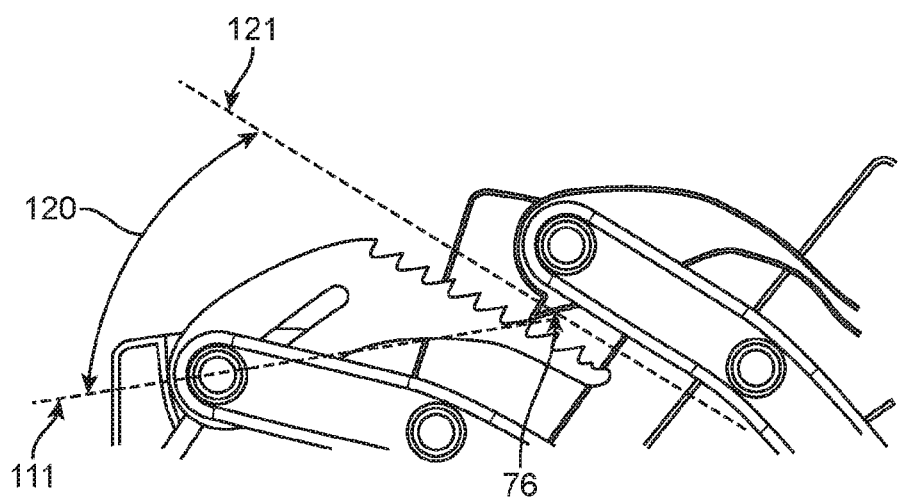

As shown in FIG. 20, a new angle 120 can be defined between a line 121 normal to the face of a tooth 76 on the first engagement member 70 and line 111 as previously described.

Figure 21:
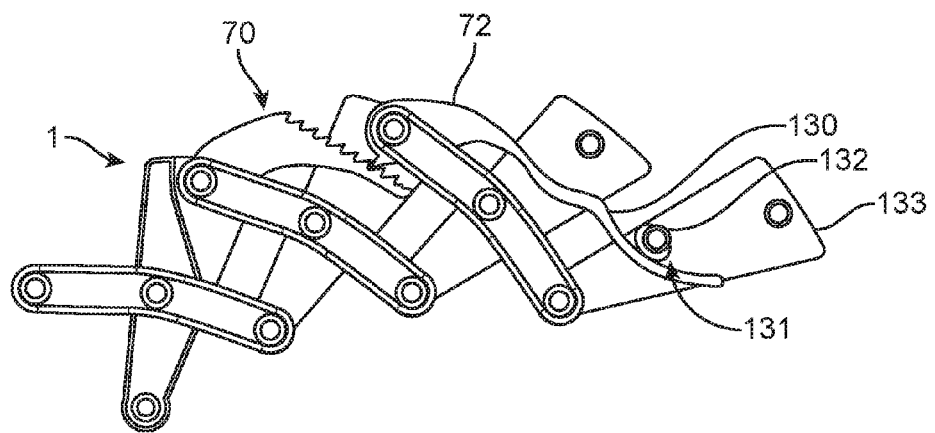

FIG. 21 illustrates yet another exemplary embodiment of a mechanism. In order to control the rotation of second engagement member 72 and therefore, angle 121, an arcuate surface 130, such as a cam surface, may be provided on second engagement member 72 as shown. The arcuate surface 130 may engage a mating surface 131, such as a post 132, disposed on a fourth link 133. The arcuate surface 130 may be provided with a profile such that angle 121 is controlled or maintained within a desirable range as structure 1 changes state. The desirable range may be between 0 degrees and 180 degrees, or more preferably between 5 degrees and 95 degrees.

Further, to help ensure engagement between the arcuate surface 120 and mating surface 121, a torsion spring may be disposed between the second engagement member 70 and second link 73 and configured to provide a torque in a direction to cause engagement between the first engagement member 70 and the second engagement member 72. As previously discussed, the torsion spring may be disposed about a post 78 on a second link 73 and its legs may be captured in a first slot provided on second engagement member 72 and a second slot provided on a second link 73.

The first engagement member 70 and second engagement member 72 may be made from a plastic material such as polycarbonate (PC), polypropylene (PP), polyethylene (PE) or another material known to one skilled in the art. The members may be injection molded, milled, laser cut, or additively manufactured using such processes as Fused-Deposition Modeling (FDM) or other process known to those skilled in the art. Additionally, the first engagement member 70 and second engagement member 72 members may be made from a metal material such as steel, stainless steel, aluminum, titanium, or another material known to those skilled in the art. The members may be injection molded, milled, laser cut, or additively manufactured using such processes as Fused-Deposition Modeling (FDM) or other process known to those skilled in the art.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A surgical access system for facilitating access through an incision to a surgical site in a patient's body, said system comprising:
    a pliable membrane having a superior end and an inferior end, the pliable membrane configured to engage and expand the incision, the pliable membrane comprising:
    a base layer; and
    a permeable membrane attached to the base layer;
    a superior retention member coupled to the superior end of the pliable membrane, wherein the superior end of the pliable membrane comprises a plurality of tabs each having a hole disposed therethrough, the hole configured to be coupled with an engagement element on the superior retention member; and
    a resilient inferior retention member coupled to the inferior end of the pliable membrane.

2. The surgical access system of claim 1, wherein the superior retention member comprises a radially expandable retention ring actuatable between a collapsed configuration, an expanded configuration, and a plurality of configurations therebetween.

3. The surgical access system of claim 2, further comprising a locking mechanism coupled to the superior retention member, the locking mechanism actuatable between a locked position and an unlocked position, wherein the locked position is configured to hold the radially expandable retention ring in a desired configuration and the unlocked position is configured to allow radial expansion or radial collapsing of the radially expandable retention ring.

4. The surgical access system of claim 1, wherein the pliable membrane further comprises a fluid channel disposed between the base layer and the permeable membrane, wherein the fluid channel is fluidly coupled to a fluid source and fluid from the fluid source is delivered to the surgical site via the permeable membrane.

5. The surgical access system of claim 1, wherein the pliable membrane further comprises a suction channel disposed between the base layer and the permeable membrane, wherein the suction channel is configured to be coupled to a vacuum source, and vacuum from the vacuum source draws fluid from the surgical site into the suction channel via the permeable membrane.

* * * * *